United States Patent
Azimi

(10) Patent No.: US 10,554,756 B2
(45) Date of Patent: Feb. 4, 2020

(54) SYSTEM AND METHOD FOR RELIABLE AND SCALABLE HEALTH MONITORING

(71) Applicant: Vital Connect, Inc., San Jose, CA (US)

(72) Inventor: Saeed Azimi, San Jose, CA (US)

(73) Assignee: VITAL CONNECT, INC., San Jose, CA (US)

( * ) Notice: Subject to any disclaimer, the term of this patent is extended or adjusted under 35 U.S.C. 154(b) by 0 days.

(21) Appl. No.: 15/673,873

(22) Filed: Aug. 10, 2017

(65) Prior Publication Data

US 2017/0366615 A1 Dec. 21, 2017

Related U.S. Application Data

(63) Continuation of application No. 13/672,119, filed on Nov. 8, 2012, now Pat. No. 9,762,673, which is a (Continued)

(51) Int. Cl.
*H04L 29/08* (2006.01)
*G06F 16/25* (2019.01)
(Continued)

(52) U.S. Cl.
CPC ............ *H04L 67/12* (2013.01); *A61B 5/1113* (2013.01); *G06F 16/252* (2019.01);
(Continued)

(58) Field of Classification Search
CPC ... H04L 67/12; H04L 67/142; G06F 17/3056; G06F 19/3412; G06F 19/34;
(Continued)

(56) References Cited

U.S. PATENT DOCUMENTS

| 5,752,917 A | 5/1998 | Fuchs |
| 6,084,513 A | 7/2000 | Stoffer |

(Continued)

FOREIGN PATENT DOCUMENTS

| CN | 1151857 | 6/1997 |
| CN | 2544684 | 4/2003 |

(Continued)

OTHER PUBLICATIONS

International Search Report and Written Opinion of the International Searching Authority for International application No. PCT/US12/61838, dated Jan. 8, 2013.

*Primary Examiner* — Franklin D Balseca
(74) *Attorney, Agent, or Firm* — Brundidge & Stanger, P.C.

(57) ABSTRACT

A health-monitoring system and method are disclosed. The health-monitoring system and method comprise a sensory system and a sensory to front-end communication (SFCM) protocol coupled to the sensory system. The health-monitoring system and method include a front-end system coupled to the sensory system and a front-end to back-end communication (FBCM) protocol coupled to the front-end system. The health-monitoring system and method include a back-end system. The SFCM protocol communicates with the front-end system using a first state awareness link and the FBCM protocol communicates with the back-end system using a second state awareness link.

17 Claims, 2 Drawing Sheets

Related U.S. Application Data continuation of application No. 13/281,153, filed on Oct. 25, 2011, now Pat. No. 9,247,004.

(51) Int. Cl.

| | | |
|---|---|---|
| *A61B 5/11* | (2006.01) | |
| *A61B 5/00* | (2006.01) | |
| *G06F 19/00* | (2018.01) | |
| *H04Q 9/00* | (2006.01) | |

(52) U.S. Cl.
CPC .......... *H04L 67/142* (2013.01); *A61B 5/0002* (2013.01); *A61B 5/0015* (2013.01); *A61B 5/0024* (2013.01); *A61B 5/6833* (2013.01); *A61B 2560/045* (2013.01); *A61B 2560/0412* (2013.01); *G06F 19/34* (2013.01); *G06F 19/3418* (2013.01); *H04Q 9/00* (2013.01); *H04Q 2209/00* (2013.01); *H04Q 2209/10* (2013.01); *H04Q 2209/40* (2013.01); *H04Q 2209/86* (2013.01)

(58) Field of Classification Search
CPC .... G06F 19/3418; G06F 19/00; G06F 16/252; H04Q 9/00; H04Q 2209/00; H04Q 2209/10; H04Q 2209/40; H04Q 2209/70; H04Q 2209/86; A61B 5/1113; A61B 5/0002; A61B 5/0015; A61B 5/0024; A61B 5/6833; A61B 2560/0412; A61B 2560/045; G16H 40/40
See application file for complete search history.

(56) References Cited

U.S. PATENT DOCUMENTS

| | | | | |
|---|---|---|---|---|
| 6,393,341 | B1 | 5/2002 | Lawrence et al. | |
| 8,327,354 | B1 * | 12/2012 | Magenheimer | G06F 9/45554 711/206 |
| 8,448,027 | B2 * | 5/2013 | Elnozahy | G06F 11/3672 714/25 |
| 8,686,861 | B2 * | 4/2014 | Chung | G01S 5/0018 340/10.4 |
| 8,922,650 | B2 * | 12/2014 | Clapp | G06F 16/78 348/143 |
| 8,937,930 | B2 * | 1/2015 | Sprigg | G06F 9/4411 370/338 |
| 9,247,004 | B2 * | 1/2016 | Azimi | H04L 67/12 |
| 9,656,092 | B2 * | 5/2017 | Golden | A61B 5/7465 |
| 9,762,673 | B2 * | 9/2017 | Azimi | H04L 67/12 |
| 2004/0167465 | A1 * | 8/2004 | Mihai | A61B 5/0002 604/67 |
| 2006/0122864 | A1 | 6/2006 | Gottesman et al. | |
| 2006/0230124 | A1 | 10/2006 | Belfiore et al. | |
| 2006/0293571 | A1 | 12/2006 | Bao et al. | |
| 2007/0174716 | A1 | 7/2007 | Erdtmann et al. | |
| 2008/0052757 | A1 | 2/2008 | Gulati | |
| 2008/0065416 | A1 * | 3/2008 | Mazar | A61B 5/0031 705/2 |
| 2008/0097909 | A1 | 4/2008 | Dicks et al. | |
| 2008/0119705 | A1 * | 5/2008 | Patel | G06F 19/3418 600/347 |
| 2009/0054737 | A1 | 2/2009 | Magar et al. | |
| 2009/0058635 | A1 | 3/2009 | LaLonde et al. | |
| 2009/0115628 | A1 | 5/2009 | Dicks et al. | |
| 2009/0119658 | A1 | 5/2009 | Thoon et al. | |
| 2010/0045425 | A1 * | 2/2010 | Chivallier | A61B 5/0002 340/5.8 |
| 2010/0049006 | A1 | 2/2010 | Magar et al. | |
| 2010/0056875 | A1 | 3/2010 | Schoenberg et al. | |
| 2010/0076412 | A1 | 3/2010 | Rush et al. | |
| 2011/0178499 | A1 * | 7/2011 | Brukalo | A61B 5/0002 604/504 |
| 2012/0302841 | A1 | 11/2012 | Coressel et al. | |
| 2013/0045685 | A1 * | 2/2013 | Kiani | G08B 21/24 455/41.2 |

FOREIGN PATENT DOCUMENTS

| | | |
|---|---|---|
| JP | 2011-502369 | 1/2011 |
| WO | WO0198936 | 12/2001 |
| WO | WO2006/111878 | 10/2006 |

* cited by examiner

SYSTEM AND METHOD FOR RELIABLE AND SCALABLE HEALTH MONITORING

CROSS-REFERENCE TO RELATED APPLICATION

This application is Continuation of U.S. application Ser. No. 13/672,119, filed Nov. 8, 2012; which is a Continuation of U.S. application Ser. No. 13/281,153, filed Oct. 25, 2011, entitled "SYSTEM AND METHOD FOR RELIABLE AND SCALABLE HEALTH MONITORING," which is incorporated herein by reference.

FIELD OF THE INVENTION

The present invention relates to health monitoring, and more particularly, to a system and method for reliable and scalable health monitoring.

BACKGROUND

Monitoring systems are used in a variety of applications including monitoring the health of individuals. Conventional health monitoring systems typically include a combination of underlying systems or device components such as sensors, recording systems, and storage units. Software is integrated with the hardware of each device component to aid the communication of data between each device component of the conventional health monitoring system.

These conventional health monitoring systems typically have predetermined hardware and software architectures for each device component. However, if one of these device components is either updated with new hardware or replaced with a different device component, the communication of data is disrupted and the software integrated with the hardware of each device component must be updated to match the new underlying device configuration of the conventional health monitoring system which is time consuming and costly. In some instances, the new underlying device configuration is incompatible or it is impossible to update the software to restore the communication of data and so the entire health monitoring system must be replaced.

In addition, the communication of data within the health monitoring system can be interrupted due to a limitation of the technology such as one device component being out of the operating range of another device component or power source failures. In this situation, the communication of data is retried until it is received or the transmittance is terminated. As a result, the communication of data between the device components is not independent of the underlying health monitoring system infrastructure.

These issues limit the interchangeability and scalability of the device components within the health monitoring system. Therefore, there is a strong need for a cost-effective solution that overcomes the above issues by creating a highly reliable, fault tolerant and scalable health monitoring system that contains a clear communication path between device components that is completely independent of underlying architecture. The present invention addresses such a need.

SUMMARY OF THE INVENTION

A health-monitoring system and method are disclosed. In a first aspect, the health-monitoring system comprises a sensory system and a sensory to front-end communication (SFCM) protocol coupled to the sensory system. The health-monitoring system includes a front-end system coupled to the sensory system and a front-end to back-end communication (FBCM) protocol coupled to the front-end system. The health-monitoring system includes a back-end system. The SFCM protocol communicates with the front-end system using a first state awareness link and the FBCM protocol communicates with the back-end system using a second state awareness link.

In a second aspect, the method comprises providing a sensory system and coupling a sensor to front-end communication (SFCM) protocol to the sensory system. The method includes coupling a front-end system to the sensory system and coupling a front-end to back-end communication (FBCM) protocol to the front-end system. The method includes coupling the front-end system to a back-end system. The method includes communicating data between the SFCM protocol and the front-end system using a first state awareness link and communicating data between the FBCM protocol and the back-end system using a second state awareness link.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

The present invention relates to health monitoring, and more particularly, to a system and method for reliable and scalable health monitoring. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A system and method in accordance with the present invention allows for a multiple sensory system that logically connects to a front-end system and in turn to a back-end system. These connections create a health-monitoring system with a clear data communication path that is independent of the underlying architecture of the health-monitoring system. By utilizing state awareness methods and state awareness links into the sensory, the front-end, and the back-end systems, a highly reliable and scalable health-monitoring system is achieved that can support a significant number of active users.

To describe the features of the present invention in more detail, refer now to the following description in conjunction with the accompanying Figures.

Figure 1:
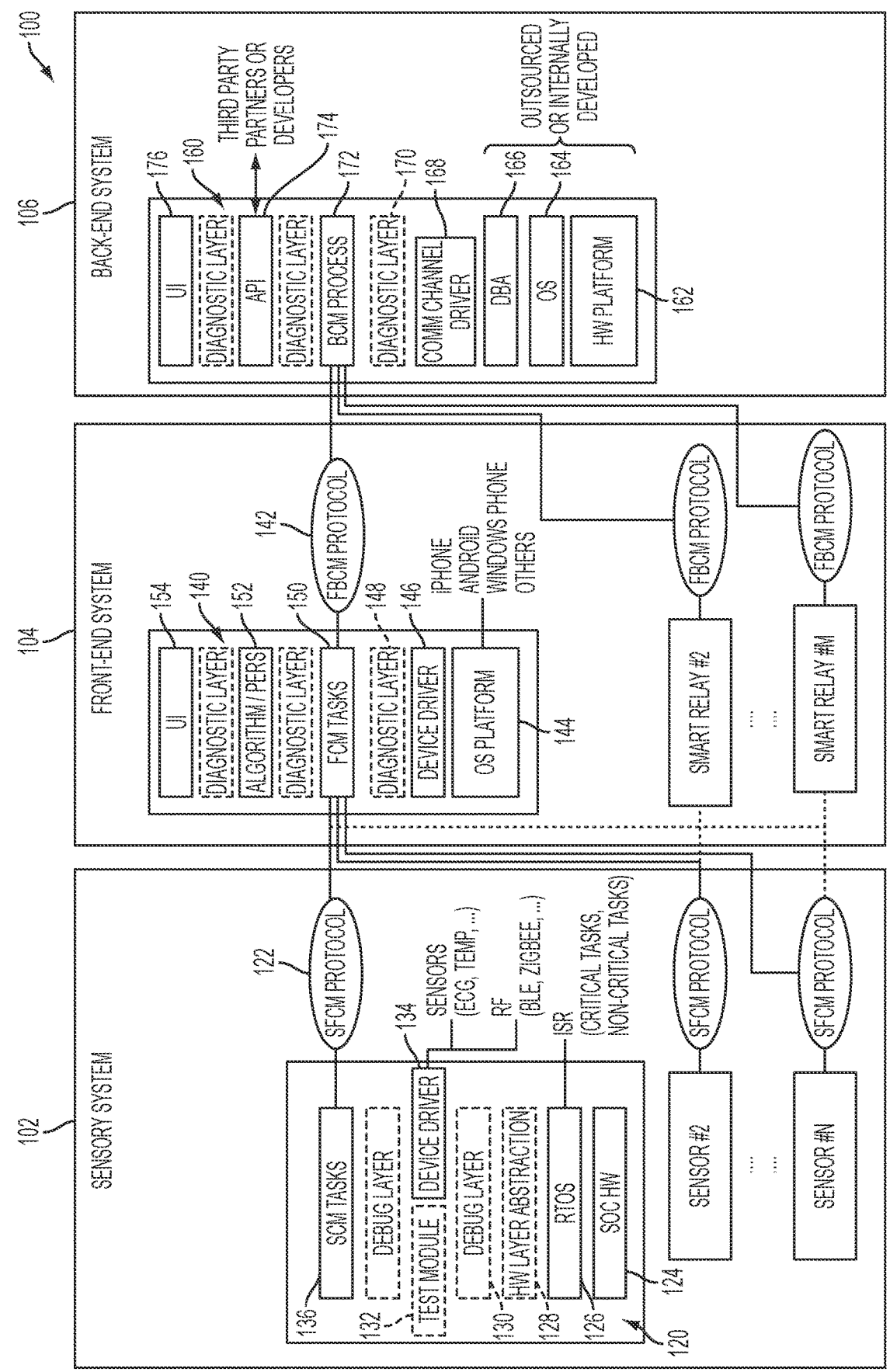
FIG. 1 illustrates a health monitoring system in accordance with an embodiment.

Health-Monitoring System:

FIG. 1 illustrates a health-monitoring system 100 in accordance with an embodiment. The health-monitoring system 100 includes a sensory system 102, a front-end system 104 coupled to the sensory system 102, and a back-end system 106 coupled to the front-end system 104. The sensory system 102 includes a sensor 120 coupled to a sensory to front-end communication (SFCM) protocol 122. The front-end system 104 includes an interface 140 coupled to a front-end to back-end communication (FBCM) protocol 142 and the back-end system 106 includes a server 160.

The SFCM protocol 122 communicates with the front-end system 104 using a first state awareness link and the FBCM protocol 142 communicates with the back-end system using a second state awareness link. These state awareness links enable each system within the health-monitoring system 100 to detect and understand the underlying architecture of each other system and reestablish communications between systems.

One of ordinary skill in the art readily recognizes that the state awareness links can detect and understand numerous types of data including but not limited to state awareness information, transmitted data and the conditions or states of both the transmitting and receiving devices. Data related to the conditions or states of both the transmitting and receiving devices includes but is not limited to information pertaining to the device types, revisions, modes and data statuses.

Device type information may include the number of physical hardware sensors present and the way in which sensory data is combined together to form a final data format. Device revision information may include the data format versions of the sensory hardware or firmware or protocol stack id. Device mode information may include retry, error recovery, data loss, normal, alert, waiting for upgrade, and require customer profile modes. Data status information may include fully encrypted data, critical data profiles or broken but recoverable data.

One of ordinary skill in the art readily recognizes that the sensor 120, the interface 140 and the server 160 can include a variety of devices including but not limited to wireless sensors, collections of body vital sign metrics in patch form, smart relays, cell phones, mobile devices, applications, and database servers and that would be within the spirit and scope of the present invention.

The sensor 120 includes a system on-a-chip hardware (SOC HW) 124, a real-time operating system (RTOS) 126, a hardware layer abstraction 128, at least one debug layer 130, a test module 132, a device driver 134, and at least one sensory communication (SCM) task 136 coupled to the SFCM protocol 122. In one embodiment, the at least one SCM task 136 includes at least one computational task. One of ordinary skill in the art readily recognizes that the SOC HW 124, the RTOS 126, the hardware layer abstraction 128, the at least one debug layer 130, the test module 132, the device driver 134 and the at least one SCM task can be coupled to each other in a variety of different ways and configurations or can be stand-alone devices and that would be within the spirit and scope of the present invention.

The interface 140 includes an operating system (OS) platform 144, a device driver 146, at least one diagnostic layer 148, at least one front-end communication (FCM) task 150 coupled to the FBCM protocol 142, a personal emergency response system (PERS) 152, and a user interface (UI) 154. The OS platform 144 can support a variety of operating systems including but not limited to independent OS platforms. One of ordinary skill in the art readily recognizes that the OS platform 144, the device driver 146, the at least one diagnostic layer 148, the at least one FCM task 150, the PERS 152, and the UI 154 can be coupled to each other in a variety of different ways and configurations or can be stand-alone devices and that would be within the spirit and scope of the present invention.

The server 160 includes a hardware (HW) platform 162, an operating system (OS) 164, a database administrator (DBA) 166, a communication (COMM) channel driver 168, at least one diagnostic layer 170, a BCM process 172 coupled to the FBCM protocol 142, an application programming interface (API) 174, and a user interface (UI) 176. The API 174 can support custom or partner user interfaces. One of ordinary skill in the art readily recognizes that that the HW platform 162, the OS 164, the DBA 166, the COMM channel driver 168, the at least one diagnostic layer 170, the BCM process 127, the API 174 and the UI 176 can be coupled to each other in a variety of different ways and configurations or can be stand-alone devices and that would be within the spirit and scope of the present invention.

Sensory System:

The RTOS 126 includes a variety of capabilities including but not limited to having no task deadlock so there is a forced timed out with logging, self-resetting for catastrophic recovery, abstracting all hardware registers so direct access of the bits/registers are not allowed, having error correction code (ECC) parity memory, and having datapath recovery. One of ordinary skill in the art readily recognizes that the RTOS 126 may include a variety of other capabilities and that would be within the spirit and scope of the present invention.

The at least one debug layer 130 includes a variety of capabilities including but not limited to having non-production code, simulating electrocardiogram (ECG), measuring temperature, resistance, Micro-Electrical Mechanical Systems (MEMS), and blood oxygen saturation, simulating RF stacks, and having an error injection module where the size target in the error injection mode is <10 Kbytes and the size target in full-mode is <64 Kbytes. One of ordinary skill in the art readily recognizes that the at least one debug layer 130 may include a variety of other capabilities and that would be within the spirit and scope of the present invention.

The SFCM protocol 122 is a two way communication protocol that pairs the sensory system 102 with the front-end system 104. The SFCM protocol 122 includes a variety of capabilities including but not limited to having a state awareness link, having the ability to miss and retry while setting up data communication paths, supporting multiple sensors, and supporting different versions of the same type of sensor. One of ordinary skill in the art readily recognizes that the SFCM protocol 122 may include a variety of other capabilities and that would be within the spirit and scope of the present invention.

Front-End System:

The at least one FCM task 150 includes a variety of capabilities including but not limited to communicating with the at least one SCM task 136 and the BCM process 172, having redundancy in the communication, operating with a fail-safe mechanism so an alarm occurs when a pairing status is unavailable or unreliable, buffering sensor data, buffering the BMC process 172 data commands, and logging location and date/time information. One of ordinary skill in the art readily recognizes that the at least one FCM task 150 may include a variety of other capabilities and that would be within the spirit and scope of the present invention.

The FBCM protocol 142 is a two way communication protocol that pairs the front-end system 104 with the back-end system 106. The FBCM protocol 142 includes a variety of capabilities including but not limited to having a state awareness link, having the ability to miss and retry while setting up data communication paths, supporting multiple physical links (SMS or data) in generic mode, and logging variable length data. One of ordinary skill in the art readily recognizes that the FBCM protocol 142 may include a variety of other capabilities and that would be within the spirit and scope of the present invention.

The device driver 146 includes a variety of capabilities including but not limited to having a physical link driver mapping layer to ensure the data communication path is independent of both the actual underlying architecture of the front-end system 104 and the OS platform 144, and having a unified payload architecture. One of ordinary skill in the art readily recognizes that the device driver 146 may include a variety of other capabilities and that would be within the spirit and scope of the present invention.

The at least one diagnostic layer 148 includes a variety of capabilities including but not limited to having non-production code, simulating the device driver 146 protocol, simulating the UI 154, simulating the at least one FCM task 150 for a higher level protocol, and having error injection. One of ordinary skill in the art readily recognizes that the at least one diagnostic layer 148 may include a variety of other capabilities and that would be within the spirit and scope of the present invention.

The UI 154 includes a variety of capabilities including but not limited to facilitating a user experience, having graphic and flow modules customized to the health-monitoring system 100, having user annotation, having a login procedure, and having its graphical display be programmable from the back-end system 106. One of ordinary skill in the art readily recognizes that the UI 154 may include a variety of other capabilities and that would be within the spirit and scope of the present invention.

Back-End System:

The BMC process 172 includes a variety of capabilities including but not limited to receiving secure data from the front-end system 104, authenticating and encrypting data and the data communication path, aggregating data, sending outbound messages, and initiating data communication path connections with the front-end system 104 or the sensory system 102. One of ordinary skill in the art readily recognizes that the BMC process 172 may include a variety of other capabilities and that would be within the spirit and scope of the present invention.

The UI 176 includes a variety of capabilities including but not limited to graphically displaying sensory or customer information, having a login procedure, having user annotation, having a user profile and account information, supporting temporary or trial periods, having an administrative procedure, and having reporting capability. One of ordinary skill in the art readily recognizes that the UI 176 may include a variety of other capabilities and that would be within the spirit and scope of the present invention.

The HW platform 162 includes a variety of capabilities including but not limited to having continuous 24/7 operation and having a redundant geographical system within and across suppliers. One of ordinary skill in the art readily recognizes that the HW platform 162 may include a variety of other capabilities and that would be within the spirit and scope of the present invention.

The OS 164 includes a variety of capabilities including but not limited to supporting independent OS platforms and the DBA 166 includes a variety of capabilities including but not limited to having independent database management architecture, being scalable, fault tolerant and distributed, and supporting millions of nodes. One of ordinary skill in the art readily recognizes that the OS 164 and the DBA 166 may include a variety of other capabilities and that would be within the spirit and scope of the present invention.

The COMM channel driver 168 includes a variety of capabilities including but not limited to supporting physical links to the front-end system 104 that are independent of the HW platform 162 and the at least one diagnostic layer 170 includes a variety of capabilities including but not limited to having isolation and simulation capability. One of ordinary skill in the art readily recognizes that the COMM channel driver 168 and the at least one diagnostic layer 170 may include a variety of other capabilities and that would be within the spirit and scope of the present invention.

Figure 2:
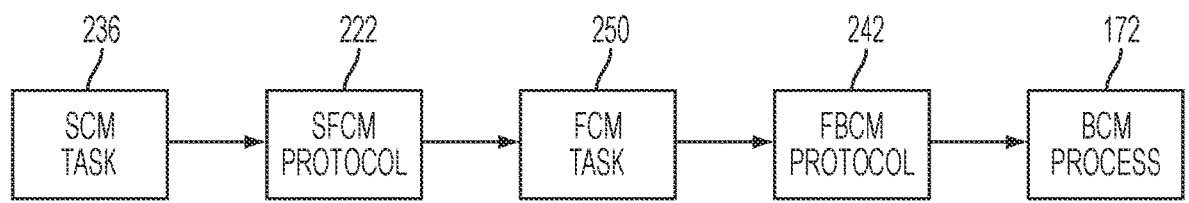
FIG. 2 illustrates a block diagram of a data communication path in accordance with an embodiment.

Data Communication Path:

The health-monitoring system 100 communicates data from the sensory system 102 to the back-end system 106 through two sets of protocols which are the SFCM protocol 122 and the FBCM protocol 142. FIG. 2 illustrates a block diagram 200 of a data communication path in accordance with an embodiment. In the block diagram 200, data is measured by the at least one SCM task 236 and communicated to the SFCM protocol 222 which connects the at least one SCM task 236 to the at least one FCM task 250.

As a result, the SFCM protocol 222 allows the at least one FCM task 250 to be aware of the state of the at least one SCM task 236 and the data measured by the underlying sensory system 102. The data is then communicated to the at least one FCM task 250, in turn to the FBCM protocol 242, and finally to the BCM process 172 to complete the data communication path from the sensory system 102 to the back-end system 106. The BCM process 172 can receive data from different paths that are created by the underlying system architectures. Therefore, the back-end system 106 is also aware of the state of both the sensory system 102 and the front-end system 104.

After the data is measured by the at least one SCM task 236, it is encrypted and secured before it is communicated to the SFCM protocol 222. As a result, the secure data is not visible to the various layers of the underlying systems within the health-monitoring system 100. One of ordinary skill in the art readily recognizes that a variety of encryption methodologies can be utilized to secure the data and that would be within the spirit and scope of the present invention.

As above described, the system and method allow for a multiple sensory system that logically connects to a front-end system and in turn to a back-end system to create a health-monitoring system with a clear data communication path that is independent of the underlying architecture of the health-monitoring system. By implementing state awareness methods and state awareness links into the sensory, the front-end, and the back-end systems, a system and method in accordance with the present invention achieves a highly reliable, fault tolerant and scalable health-monitoring system that can support a significant number of active users.

A health monitoring system and method has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk—read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A front-end health-monitoring device, comprising:
a smart relay device that includes a front-end communication (FCM) task, a diagnostic layer, and user interface (UI),
wherein the FCM task is coupled to a transceiver using a sensory to front-end communication (SFCM) protocol of a sensory health-monitoring device,
wherein the FCM task performs: communicating with a sensory communication (SCM) task, communicating with a back-end communication (BCM) process, operating with a fail-safe mechanism so an alarm occurs when a pairing status is unavailable or unreliable, buffering sensor data, buffering a data command of the BCM process, and logging location and date/time information,
wherein the transceiver using the SFCM protocol performs a system state detection and a system communication between the sensory health-monitoring device and the front-end health-monitoring device, and
wherein the diagnostic layer includes: simulating a device driver protocol, simulating the UI, simulating the FCM task that includes communicating with the SCM task and the BCM process, and error injection; and
a transceiver using a front-end to back-end communication (FBCM) protocol coupled to the FCM task,
wherein the transceiver using the FBCM protocol performs a system state detection and a system communication between a back-end health-monitoring device and the front-end health-monitoring device.

2. The device of claim 1, wherein the SCM task within the sensory health-monitoring device includes a computation task that processes biometric data measured by the sensory health-monitoring device.

3. The device of claim 2, wherein the transceiver using the SFCM protocol receives the processed biometric data from the SCM task and transports the processed biometric data to the FCM task within the front-end health-monitoring device.

4. The device of claim 3, wherein the transceiver using the FBCM protocol receives the processed biometric data from the FCM task and transports the processed biometric data to the BCM process within the back-end health-monitoring device.

5. The device of claim 1, wherein the transceiver using the SFCM protocol further performs encrypted communications between the sensory health-monitoring device and the front-end health-monitoring device.

6. The device of claim 1, wherein the transceiver using the FBCM protocol further performs encrypted communications between the back-end health-monitoring device and the front-end health-monitoring device.

7. The device of claim 1, wherein the sensory health-monitoring device includes a debug layer.

8. A method for monitoring health of a body, by a smart relay device that includes a front-end communication (FCM) task, a diagnostic layer, and user interface (UI), the method comprising:
communicating, by the FCM task of the smart relay device, with a sensory communication (SCM) task via a transceiver using front-end communication (SFCM) protocol of a sensory health-monitoring device;
communicating, by the FCM task, with a back-end communication (BCM) process of a back-end health-monitoring device;
operating, by the FCM task, with a fail-safe mechanism so an alarm occurs when a pairing status is unavailable or unreliable; buffering, by the FCM task, sensor data;
buffering, by the FCM task, a data command of the BCM process;
logging, by the FCM task, location and date/time information;
receiving data from the transceiver using the SFCM protocol using a first state awareness link; transmitting data from a transceiver using a front-end to back-end communication (FBCM) protocol of the smart relay device to the back-end health-monitoring device using a second state awareness link; and
simulating: a device driver protocol, the UI, the FCM task that includes communicating with the SCM task and the BCM process, and error injection.

9. The method of claim 8, wherein the SCM task within the sensory heath-monitoring device includes a task for processing data measured by the sensory health-monitoring device.

10. The method of claim 9, wherein:
the transceiver using the SFCM protocol receives the processed data from the SCM task; and
the processed data is received by the FCM task from the transceiver using the SFCM protocol.

11. The method of claim 10, further comprising:
receiving the processed data by the transceiver using the FBCM protocol from the FCM task; and
transporting the processed data to the BCM process of the back-end health-monitoring device.

12. The method of claim 8, further comprising:
receiving, by the FCM task, detected state awareness information of the sensory health-monitoring device through the first state awareness link.

13. The method of claim 8, further comprising:
detecting state awareness information of a front-end health monitoring device; and
communicating the detected state awareness information to the BCM process through the second state awareness link.

14. The method of claim 13, further comprising:
transmitting data to the FCM task and in turn to the FBCM protocol and in turn to the BCM process utilizing the detected state awareness information.

15. The method of claim 14, further comprising:
receiving data by the FCM task from communicating paths that do not depend on underlying architectures of the sensory health-monitoring device, front-end health-monitoring device, and back-end health-monitoring device.

16. The method of claim 13, further comprising:
establishing a connection with either the sensory health-monitoring device or the back-end health monitoring device by utilizing the detected state awareness information.

17. The method of claim 8,
wherein the SFCM protocol is a two-way communication protocol between the sensory health-monitoring device and a front-end health-monitoring device, and
wherein the FBCM protocol is a two-way communication protocol between the front-end health-monitoring device and the back-end health-monitoring device.

* * * * *